United States Patent
Lao, Jr. et al.

(10) Patent No.: US 10,327,452 B2
(45) Date of Patent: Jun. 25, 2019

(54) PREPARATION AND COMPOSITION OF MEDIUM CHAIN TRIGLYCERIDES CONTAINING SUBSTANTIAL AMOUNT OF LAURIC ACID

(71) Applicant: Dean A. Lao, Jr., Quezon (PH)

(72) Inventors: Dean A. Lao, Jr., Quezon (PH); Sonia D. Salvador, Quezon (PH); Glenn C. Apostol, Quezon (PH)

( * ) Notice: Subject to any disclaimer, the term of this patent is extended or adjusted under 35 U.S.C. 154(b) by 0 days.

(21) Appl. No.: 15/324,298

(22) PCT Filed: Jul. 25, 2014

(86) PCT No.: PCT/PH2014/000015
§ 371 (c)(1),
(2) Date: Jan. 6, 2017

(87) PCT Pub. No.: WO2016/007026
PCT Pub. Date: Jan. 14, 2016

(65) Prior Publication Data
US 2017/0172170 A1  Jun. 22, 2017

(30) Foreign Application Priority Data
Jul. 10, 2014 (PH) .................... 1-2014-000195

(51) Int. Cl.
| | |
|---|---|
| *A23D 9/04* | (2006.01) |
| *A23L 29/20* | (2016.01) |
| *A23D 9/00* | (2006.01) |
| *A61K 31/20* | (2006.01) |
| *C11B 3/04* | (2006.01) |
| *C11B 7/00* | (2006.01) |
| *C11C 3/04* | (2006.01) |
| *C11C 3/06* | (2006.01) |
| *C11C 1/00* | (2006.01) |

(52) U.S. Cl.
CPC .............. *A23D 9/04* (2013.01); *A23D 9/00* (2013.01); *A23L 29/20* (2016.08); *A61K 31/20* (2013.01); *C11B 3/04* (2013.01); *C11B 7/00* (2013.01); *C11C 1/005* (2013.01); *C11C 3/04* (2013.01); *C11C 3/06* (2013.01); *A23V 2002/00* (2013.01)

(58) Field of Classification Search
CPC .. A23D 9/04; A23D 9/00; A23L 29/20; A23K 31/20; C11B 3/04; C11B 7/00; C11C 1/005; C11C 3/04; C11C 3/06
USPC ....................................... 514/558
See application file for complete search history.

(56) References Cited

U.S. PATENT DOCUMENTS

| | | | |
|---|---|---|---|
| 2,238,442 A | 4/1941 | Drew | |
| 6,835,750 B1 | 12/2004 | Henderson | |
| 7,470,445 B2 | 12/2008 | Takeuchi et al. | |
| 8,586,060 B2 | 11/2013 | Brinkmann | |
| 2004/0157766 A1* | 8/2004 | Embil .............. | A61K 8/02 514/1 |
| 2010/0119684 A1 | 5/2010 | Santana et al. | |
| 2012/0315369 A1 | 12/2012 | Kester et al. | |
| 2013/0017278 A1 | 1/2013 | Keller | |

FOREIGN PATENT DOCUMENTS

| | | |
|---|---|---|
| EP | 0376628 A2 | 7/1990 |
| EP | 0923317 A1 | 6/1999 |
| EP | 2636307 A1 | 9/2013 |
| GB | 879211 A | 10/1961 |
| JP | 2004008165 A | 1/2004 |
| JP | 2009142185 A | 7/2009 |
| WO | WO-2008002643 A2 | 1/2008 |
| WO | WO-2013126990 A1 | 9/2013 |

OTHER PUBLICATIONS

International Search Report and Written Opinion of the ISA for PCT/PH2014/000015, ISA/EPO, Rijswijk, dated May 1, 2015.
Lindqvist, B., Sjögren, I., Nordin, R., "Preparative fractionation of triglyceride mixtures according to acyl carbon number, using hydroxyalkoxypropyl Sephadex", Journal of Lipid Research, Jan. 1974; 15 (1): pp. 65-73.
Marten, B., Pfeuffer, M., Schrezenmeir, J., "Medium-chain triglycerides", International Dairy Journal 16 (2006), pp. 1374-1382.
"GRAS Notice (GRN) No. 449", http://www.fda.gov/Food/FoodIngredientsPackaging/GenerallyRecognizedasSafeGRAS/GRASListings/default.htm, retrieved Dec. 27, 2016, 28 pp.
Cosmetic Ingredient Review (CIR) Expert Panel. Annual review of cosmetic ingredient safety assessments—200112002.International Journal of Toxicology; 22(Suppl 1):1-35 2003.
Traul KA, Driedger A, Ingle DL, Nakhasi D. Review of the toxicologic properties of medium-chain triglycerides. Food Chem Toxicol. Jan. 2000;38(1):79-98.

* cited by examiner

*Primary Examiner* — Yevgeny Valenrod
(74) *Attorney, Agent, or Firm* — Harness, Dickey & Pierce, P.L.C.

(57) ABSTRACT

The present invention pertains to an efficient and large-scale process to produce a medium-chain triglyceride composition with >95% content for C8 (caprylic acid), C10 (capric acid) and C12 (lauric acid), with the content of lauric acid at about 5% or more. The process involves fractionation of fatty acid methyl esters, which are mainly derived from coconut or palm kernel, their esterification to glycerol to synthesize medium-chain triglycerides, and refining them to significantly increase purity and make them fit for human consumption. Such composition can have important uses in food and its preparation, health supplements, cosmetics, and medicine, among others.

12 Claims, 2 Drawing Sheets

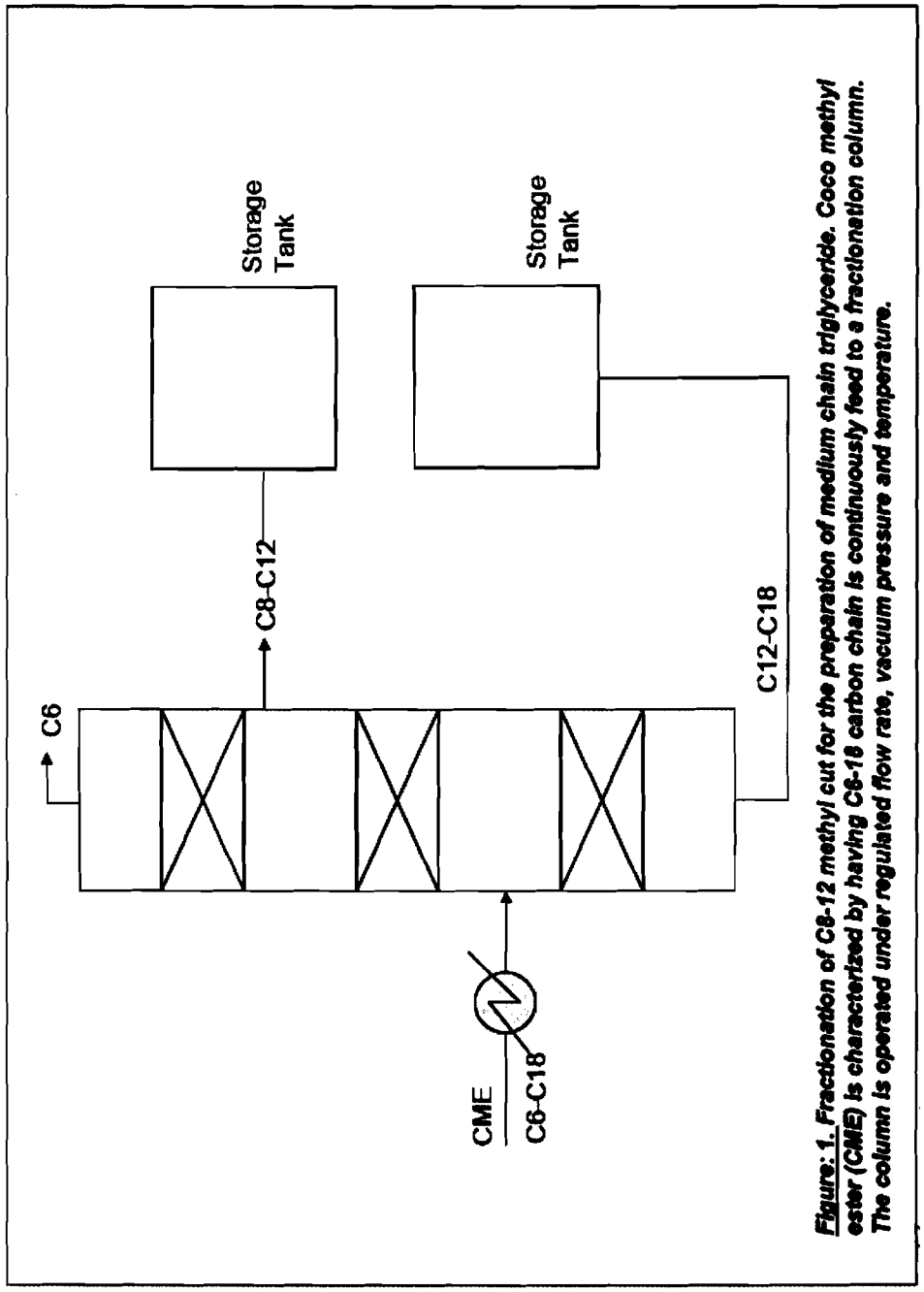

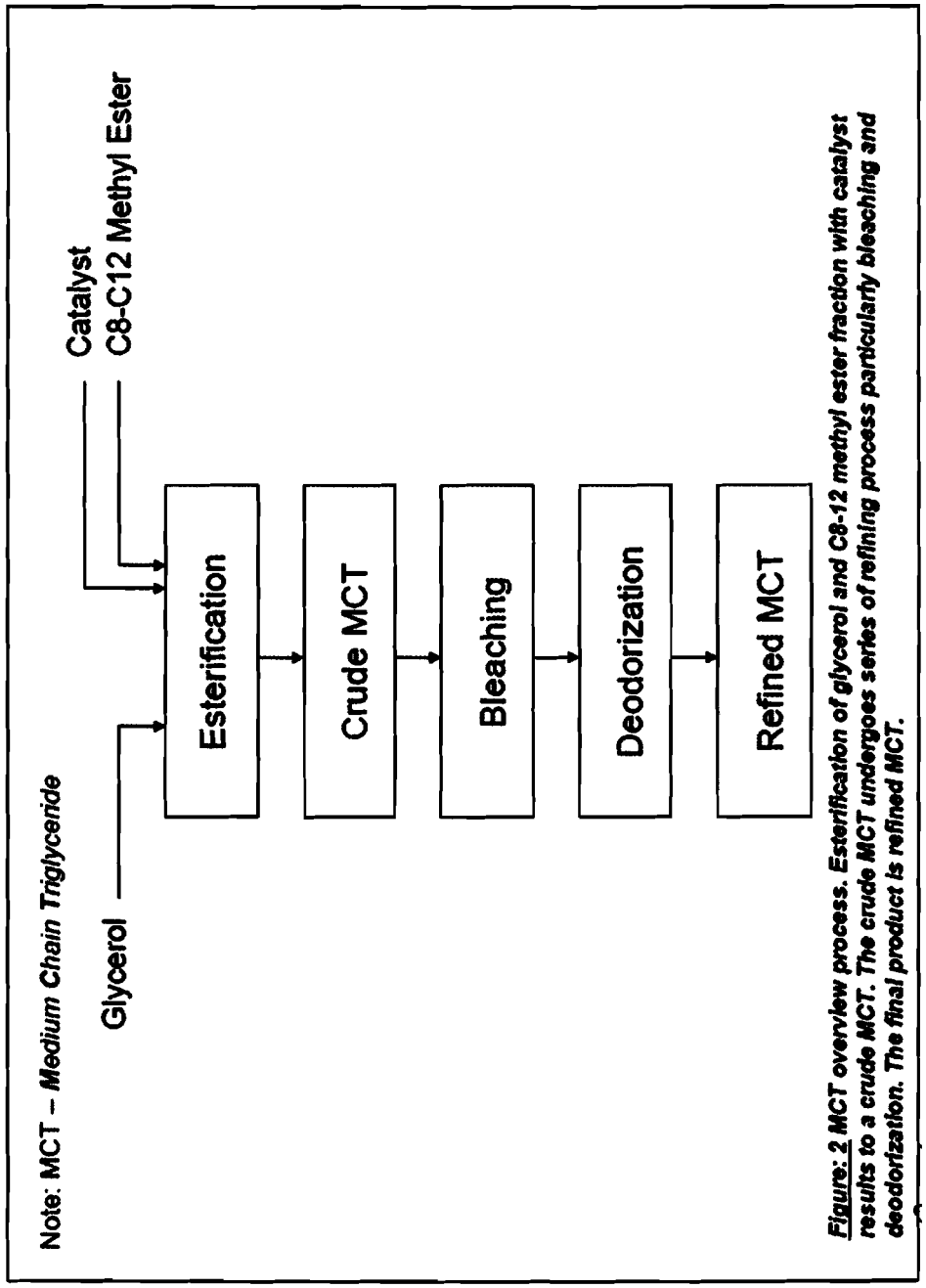
Figure 2 MCT overview process. Esterification of glycerol and C8-C12 methyl ester fraction with catalyst results to a crude MCT. The crude MCT undergoes series of refining process particularly bleaching and deodorization. The final product is refined MCT.

PREPARATION AND COMPOSITION OF MEDIUM CHAIN TRIGLYCERIDES CONTAINING SUBSTANTIAL AMOUNT OF LAURIC ACID

CROSS-REFERENCE TO RELATED APPLICATIONS

This application is a 371 U.S. National Stage of International Application No. PCT/PH2014/000015, filed Jul. 25, 2014, which claims the benefit of Philippinese Patent Application No. 1-2014-000195, filed Jul. 10, 2014. The entire disclosures of the above applications are incorporated herein by reference.

TECHNICAL FIELD

This present invention relates to the field of oils and fats, in particular to the composition of medium-chain triglycerides (MCTs) and methods of its production.

BACKGROUND OF THE INVENTION

Medium-chain triglycerides are esters derived from glycerol and 3 fatty acids with 8 to 12 carbon chain length. The main fatty acid components are caprylic acid (C8), capric acid (C10) and lauric acid (C12).

MCTs are very useful. Commercially, MCTs are utilized in the preparation of food as chemical intermediate in food additives. It is also used in the production of baked goods, beverages, chewing gum, confectionaries and frostings, dairy product analogues, fats & oils, frozen dairy desserts, processed fruits, snack foods, adult nutritionals, cheese spreads and soft candies. Functionally, it acts as, among others, emulsifier, energy source, formulation aid, lubricant, release agent, nutrition supplement, processing aid, solvent, vehicle, stabilizer, thickener, surface finishing agent, texturizer and emollient for cosmetics (US FDA 2014). On health, the benefits of MCTs as food includes reduction of intestinal injury, protection from hepatoxicity, anti-inflammation, reduced cholesteronemia and hyperglycemia (Martens et al. 2006).

As the benefits of MCTs are being realized, several additional uses are being discovered. Patent EP0923317 described MCTs in an energy or sports drink, especially designed to substitute body fluid, carbohydrates, lipids, amino acids and mineral ions during periods of heavy endurance exercise. In addition to carbohydrates, L-carnitine, mineral ions and amino acids with minor amounts of fruit juice concentrates and artificial flavors, it contains significant amount of lipid, consisting of glycerol esterified with either oleic, capric acid or caprylic acid or any combination of capric acid, caprylic acid or saturated lauric acid. Another use permits the stable integration of MCTs that optimizes the health benefit of MCTs, including its easy digestibility, greater availability of energy and other benefits. Patent US 20100119684 A1 describes food compositions incorporating MCTs, comprising 2-10% of the food composition. The inclusion of the MCT component permits increased amount of MCT to be successfully and stably incorporated into the food compositions. In addition, Patent U.S. Pat. No. 7,470,445 B2 described oil or fat composition composed chiefly of triglyceride enriched with MCTs. The oil or fat composition is low in body fat accumulation, has equal cooking properties with conventional edible oils and has good flavor and high safety (Traul et al. 2000).

An emerging use of MCTs is their therapeutic potential for neurodegenerative disorders. Patent U.S. Pat. No. 6,835,750 B1 disclosed the use of MCTs for the treatment and prevention of Alzheimer's disease and other diseases resulting from reduced neuronal metabolism. This patent demonstrates an improvement in cognitive ability upon treatment with MCTs. Recently, an MCT preparation has been disclosed to improve and maintain brain function using a composition comprising an effective amount of coconut oil and an effective amount of MCTs (US 20130017278 A1).

MCTs are also being actively studied in cosmetics. Patent U.S. Pat. No. 8,586,060 B2 proposes a cosmetic or pharmaceutical preparation as vegetable replacement for Vaseline. Being triglycerides of the MCTs, it offers different physical characteristics than ordinary oils. It has lower viscosity providing a medium for fast spreading when used as skin emollient and is non-sticky or non-greasy on the skin. Triglycerides, particularly MCTs, for cosmetic applications are safe with regards to the present practices of use and concentration as concluded by the Cosmetic Ingredient Review (CIR) Expert Panel (2003). Generally, MCT oil is regarded as GRAS (Generally Regarded as Safe) under the US C.F.R. Title 21 Part 170 and granted by the US Food and Drug Administration.

Of particular to the present invention is the enriched presence of C12 (lauric acid) as contained in the composition. Compared with other MCTs, lauric acid has particular uses. The resulting MCT of the present invention involves a composition that is enriched with substantial lauric acid, which is useful as food supplement, salad oil, frying and cooking oil, in food preparations, as well as for cosmetics, cosmeceutical and pharmaceutical purposes. It can also be prepared into a suitable formulation and as compositional ingredient in food preparations. It can act as, but not limited to, solvent, emulsifier, energy source, formulation aid, food grade lubricant, release agent, nutrition supplement, processing aid, solvent, vehicle, stabilizer, thickener, surface finishing agent, texturizer and emollient for cosmetics.

Having substantial lauric acid, a MCT composition can act as food supplement to be taken orally, about 1 to 2 tablespoons daily. It is flavor-free, is a quick and instant source of energy, an alternative fuel for the brain giving enhanced alertness, and as a natural antimicrobial because as lauric acid has been proven to have such property.

In addition, the higher amount of lauric acid provides synergy with C8 and C10 acids as antimicrobial, anti-viral and anti-fungal bioactivity and can be used as natural self-preservative. As such it finds special uses in the cosmetic & toiletries, cosmeceutical and pharmaceutical industries (Marten et al. 2006).

Another example of the use of the MCTs with substantial lauric acid is the preparation of ready mix oil concentrate for hot coffee and other liquid preparations. The ready mix MCT Oil with substantial lauric acid is prepared by adding about 20% of emulsifier blend of distilled monoglycerides of oleic acid and polyethoxylated sorbitan esters. It produces a stable mixture with no floating MCT oil when added into hot coffee or similar liquid preparations.

Moreover, the present invention involves the generation of MCTs which provide several advantages such as firmness, which makes it useful as thickeners or gellants for topical application and cosmetology, longer shelf-life, resilience to rancidity and better palatability.

Also, in cases that lauric acids are cited in compositions, inclusions of significant amount of non-MCFAs are usually noted, such as myristic acid (GB879211, JP2009142185).

This could lose the benefits of MCTs in general, especially its usefulness in food preparation and in bioactive applications.

In addition to products, the present invention offers a more efficient method of producing and manufacturing MCT with substantial lauric acid content. As typically known in the art, majority of commercial MCT's are obtained by esterifying glycerol and C8 to C12 fatty acids (U.S. Pat. No. 2,238,442, WO2013126990A1). This is done in the presence of acid catalyst at temperatures ranging from 140° C. to 260° C. or with the use of an enzyme such as lipase at lower temperatures from 40° C. to 90° C.

Conventional MCT contains 50% to 70% of C8 and 30% to 50% of C10, with 2% or less of C12 and 3% or less of C6 (caproic acid). The purpose of the invention is to establish a manufacturing process of a MCT containing C8 (caprylic), C10 (capric) and substantial amount of C12 (lauric) acid via esterification of fatty acid methyl esters derived from coconut and/or palm kernel oil. In this case, the preferred feedstock is fatty acid methyl esters that are more stable and non-corrosive, thus requiring manufacturing equipment and parameters that are easier to maintain and operate. As a disadvantage, this process of producing MCT Oil via fatty acid methyl esters will result to methanol as by product, which is known to be toxic. This invention thus also presents an effective distillation and deodorization process that would ensure removal of methanol in the product.

In contrast to prior art, the resulting MCT Oil from the said process using fatty acid methyl esters contains substantial C12 esterified with glycerol. Conventional MCT process is prepared using fatty acids having 2% of lauric acid. Moreover, the new MCT Oil will contain majority of C8, C10 and C12 where C12 comprise from 2-70%, with small amounts of C6 and C14. While MCT Oil from conventional process has also C8, C10 & C12 it has lesser amount of C12.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention was indicated in the claims.

SUMMARY OF THE INVENTION

The present invention relates to the synthesis for commercial production of a medium chain triglycerides derived by esterifiying' glycerol with fatty acid methyl esters and/or fatty acids coming from coconut oil and/or palm kernel oil. The said fatty acid methyl esters or fatty acids are manufactured by transesterification or splitting process. The resulting fatty acid methyl esters are further fractionated to get the C8-12 fractions which are then used to make the final medium chain triglycerides. The C8-12 fraction has C8 content of 13-45%, C:10 of 8-35% and C:12 of 2-70%. The C8-12 fraction contains C6 (caproic) of less than 2% and C14 (myristic) of 8% or less.

Such composition leads to the use of the derived MCT with substantial lauric acid content to be useful as food supplement, food preparations, salad oil, frying and cooking oil, as well as for cosmetics, cosmeceutical and pharmaceutical uses. Preferably, it can be very useful as as a composition ingredient, health supplement and functional oil in various food preparations.

As the process of production will generate methanol, a method of removing such contaminant is further presented to generate a safe and edible MCT Oil.

SUMMARY OF FIGURES AND DRAWINGS

FIG. 1 shows the fractionation process of C8-12 methyl esters fraction. Coco methyl ester (CME) is continuously fed into a fractionation column operated at high temperatures, vacuum pressure and at regulated flow rate.

FIG. 2 shows the overall process of preparing a MCT by the reaction of glycerol and C8-12 methyl ester fraction. The crude MCT goes into series of refining process to make it edible particularly bleaching and deodorization process.

DESCRIPTION OF THE INVENTION

The present invention provides entirely a new MCT composition with substantial lauric acid content. It also provides an alternate process of direct esterification of fatty acid methyl esters and glycerol under catalytic condition for the production of MCT. Using a continuous or semi-continuous process or by batch processing, glycerol is reacted with C8-12 methyl ester fraction and refined glycerin at about 200° C.-220° C. with partial condenser to reflux the methyl esters during the course of reaction and total condenser to continually remove reaction by product such as methanol (FIG. 2).

The C8-12 methyl ester fraction is derived from the fractionation of whole cut coconut methyl ester and it is accomplished by means of a distillation unit commonly referred to as a "fractionation column" known to the person skilled in the art. The fractionation column maintained at temperature of tower top at 55-65 mbar pressure at 95° C.-100° C. and column bottom temperature of 170° C.-180° C. where the short chain lengths are collected referred as C8 to C12 (C8-C12) methyl ester cut. The bottom cut is a fraction of C12-18 methyl esters in the crude form and can be further distilled or fractionated for other uses like oleochemicals and surfactants. The C8-12 methyl ester cut yields to about 16% to 18% of the total feed of coconut methyl ester and 84% to 88% of crude C12-18 methyl ester cut. The C8-12 fraction is composed of C8 (Caprylic) of 13-45%, C10 (Capric) of 8-35% and C12 (lauric) of 2-70%. The C8 to C12 alkyl group may contain C6 (Caproic) of 2% or less and C14 (myristic) of 8% or less. Preferably, the C8-12 fraction is composed of C6 1% or less, C8 of 35-45%, C10 of 25-31%, C12 of 20-30% and C14 of 0-4%. This composition is ideal for the preparation of the final MCT Oil. Alternatively, fractionation of different fatty acids or their ester can be accomplished by other means, such as using various solvents (Lindqvist et al. 1974)

The C8-12 fraction can also be prepared in a similar fractionation column using coconut fatty acids as feedstock or palm kernel fatty acids or its methyl ester derivative. The resulting cut of the C8-12 fraction should be preferably made up also of C6 of 1% or less, C8 of 35-45%, C10 of 25-31%, C12 of 20-30% and C14 of 0-4%.

The MCT oil is then prepared by reacting the C8-C12 methyl ester fractions with glycerol and subsequently purifying such (FIG. 2). The molar ratio of glycerol to the C8-12 methyl ester fraction is from 1 mole of glycerol to 3 to 4 moles of C8-C12 methyl esters, preferably at 1 mole of glycerol to: 3.3 to 3.9 moles C8-12 methyl esters. According to the present invention, the reaction is performed in the presence of a catalyst. The reaction is undertaken at 140° C. to 260° C., more preferably at 180° C. to 220° C., and most preferably within 200° C. to 220° C. under vacuum at 60 to 80 mbar with regulated nitrogen blow until conversion to triglycerides reaches 95% or higher. Alternatively, such process can also be accomplished under atmospheric condition. The methanol as result of the condensation of glycerol and methyl esters is continually condensed and removed from the reaction mixture and the excess methyl ester is allowed to reflux in order to drive the reaction toward triglyceride formations. Skilled person in the art would know the correct balance of temperature, catalyst and applied vacuum to allow faster conversion and shorter reaction time of the esterification process. The excess C8-12 methyl ester is collected and can be re-used during the esterification stage. Hydroxyl Value (OHV) is continuously monitored until the level of 5 mgKOH/gm or less is achieved, preferably between OHV of 1 to 3 is desirable.

The catalyst of the present invention was selected from inorganic acid catalyst (homogenous & heterogenous), alkaline catalyst and metal oxides catalyst. Examples of homogeneous inorganic acid catalysts include, but not limited to, H3PO4, H2SO4, sulfonic acids and derivatives like methane sulfonic acid and p-toluene sulfonic acid. Examples of alkaline catalysts include, but not limited to, sodium hydroxide, sodium or potassium methylate. Examples of heterogeneous acid based catalysts include, but not limited to, titanates like butylstannoic acid. Examples of metallic oxides or mixed metallic oxides catalysts include, but not limited to, zinc oxides, stannous oxides, chromium oxides and zirconium oxides.

In the preparation of the new MCT Oil, the preferred catalyst can be one of the following: methanesulfonic acid 70%, sodium methylate 30% and titanates of butylstannoic acid at dosage rate of 0.30% to 0.50% w/w of the total mixture.

The present invention of esterification of glycerol and C8-12 methyl ester fraction is integrated in a refinery plant in order to produce edible MCT Oil. The crude MCT resulting from the direct esterification of glycerol and C8-12 methyl esters can be characterized having unreacted C8-12 methyl esters from the excess molar ratio, traces of alcohol like methanol and higher levels of monoglycerides and diglycerides resulting from their incomplete condensation with C8-12 methyl esters.

The refinery scale plant of the present invention can be characterized by having pressure leaf filters, bleaching tanks, steam deodorizers and collection tanks. The crude MCT oil having been described to contain unreacted methyl esters and traces of methanol shall be heated to 200° C. to 220° C. under vacuum of 60 to 80 mbars with regulated nitrogen blow for about 2 hours. Majority of the unreacted methyl esters will be stripped off including residual methanol. The spent catalyst will be removed by passing the crude MCTs thru a pressure leaf filter heated at 50° C. to 60° C. and will be collected in the bleaching tank. In the bleaching tank, it will be heated to about 90° C. to 110° C. under vacuum of 60 to 80 mbar for about 30 to 60 minutes. The amount of bleaching earth and activated carbon is added, from 0.30 to 0.50% w/w of the total mixture. After the required residence time, vacuum is stopped. Spent bleaching agents are removed by passing through a pressure leaf filter at 50° C. to 60° C. In the steam deodorization, the bleached MCTs will be heated at about 170° C. to 200° C. Firstly, it will be heated at 170° C. at 4 to 8 mbars for about 2 hours. Finally, it will be heated further to 200° C. with applied vacuum of 4 to 8 mbars for another 4 hours. Stabilizer or antioxidant like citric acid is added at 100 to 200 parts per million (ppm) in the final refined MCT oil.

The present invention disclosed a large scale process of triglycerides preparation specifically MCTs from the reaction of glycerol and C8-12 methyl esters. Those skilled in the art will appreciate that there are certain oils and fats modification which lie outside of the claims of the invention, which are nonetheless obvious and would fall within the scope of the invention. For example, MCTs can be prepared with individual cuts of C8, C10 and C12 with trace amounts of C6 and C14. These individual cuts can be in the form of fatty acid methyl esters or fatty acids and blended to the desired ratios to arrive at the same MCT oil composition claimed by this current invention. Additionally, mixtures of triglycerides of capric, triglycerides of caprylic and triglycerides of lauric can be blended at varying proportions.

Commercial MCTs are prepared via esterification of fatty acids mainly C8-10 with glycerol. The C8-10 fatty acids can be from coconut oil and the very common palm kernel oil. Coconut oil has C8-10 fatty acid fraction of about 10% to 13% depending on the method and efficiency of the collection process, whereas palm kernel oil has a lower C8-10 fraction of about 7 to 9%. The present invention offers a more abundant fraction of C12 (lauric acid) is extracted in the final C8-12 fraction.

Lauric acid oil by definition is an MCT. Among known oils, coconut or palm kernel oil has the highest content of lauric acid. Coconut oil is about 45 to 52% lauric acid and palm kernel is from 43 to 48%. Both oils offer the highest fraction of C8-12 and offer wider flexibility to custom make an MCT of variable properties and form. Hence this present invention was disclosed to utilize the C8-12 fraction to prepare MCTs with substantial lauric acid.

Another preferred embodiment of the present invention is the process of esterifying a C8-12 methyl ester fraction and glycerol through a large scale commercial process of using methyl ester fractions to produce edible MCTs. Preferably, the MCT with substantial lauric acid will have C6 1% or less, C8 of 35-45%, C10 of 25-31%, C12 of 20-30% and C14 of 0-4%. The triglyceride content of 95% or higher and about 5% combined monoglycerides and diglygycerides. Ideally, it has a slip melting point 0° C. to 15° C. where it will remain liquid from room temperature and lower temperature conditions. Nutritional value per 100 ml serving size is 750 to 860 kcal, preferably about 840 kcal (15 ml serving size of 110 to 135 kcal, preferably about 130 kcal), total fat of 90 to 100 grams preferably about 93 grams (15 ml serving size 12 to 15 grams preferably about 14 grams), saturated fat of 90 to 100 grams (15 ml serving size 12 to 15 grams preferably about 14 grams), transfat, polyunsaturated fat and monosaturated fat of 0 gram each; zero to trace amount of cholesterol, sodium, potassium, total carbohydrates including fiber, soluble fiber and sugar, protein, Vit A, C, and iron; traces amount of thiamine, riboflavin, niacin; and zero to trace amount of ash, moisture and phosphorus.

Alternative Embodiments

Besides its triglyceride form, the MCT oil presented herein can be further prepared with blending of cosmetic grade thickeners/gellants to make it soft gel for skin cosmetic applications, preferably by incorporating high-purity bentonite clays, fumed silica and magnesium aluminum silicates at 3.5% w/w of the total mixtures or less.

In addition, the MCT oil presented herein can be further prepared with blending of food emulsifiers for ready mix preparations for drinks, coffee creamers, or similar liquids, preferably composed of 80% or more of MCT oil and 20% or less of food emulsifier blends, including, but not limited to, group of distilled monolglycerides of stearic acid or oleic acid, polyglycerol fatty acid esters and polyethoxylated sorbitan esters.

CITATION LIST

Patent Literature

1. EP0923317. Gordeladze J O. Energy drink. Jun. 23, 1999
2. EP2636307. Lobee H W J, Kruidenberg M B. Antimicrobial composition containing free fatty acids and method for its production. Sep. 11, 2013
3. GB879211. Crawford R V, Southern C W. Improvements in or relating to glyceride esters. Oct. 4, 1961
4. JP2009142185. Onishi K, Shono Y, Suzuki K, Toda T, Haruna H. Oil And fat composition for cream, and cream containing the same. Jul. 2, 2009
5. US2006817558. Beetham P; Beetham pPR; Gocal G; Gocal G F V; Gocal GFW; Knuth M; Knuth M E; Walker K; Walker K A. Fatty acid mixtures and use thereof. May 27, 2013
6. US20100119684A1. Santana R D et al. Food compositions incorporating medium chain triglycerides. May 13, 2010
7. US20130017278A1. Keller A. Composition and method for improving brain function. Jan. 17, 2013
8. U.S. Pat. No. 2,238,442. DREW ERNEST F.Mixed capric-caprylic esters and method of making same. Apr. 15, 1941
9. U.S. Pat. No. 6,835,750B1. Henderson S T. Use of medium chain triglycerides for the treatment and prevention of alzheimer's disease and other diseases resulting from reduced neuronal metabolism II. Dec. 28, 2004
10. U.S. Pat. No. 7,470,445B2. Takeuchi H. Oil or fat composition. Dec. 30, 2008
11. U.S. Pat. No. 8,586,060B2. Brinkmann B. Cosmetic or pharmaceutical preparation. Nov. 19, 2013

Non Patent Literature

1. Cosmetic Ingredient Review (CIR) Expert Panel. Annual review of cosmetic ingredient safety assessments—2001/2002. *International Journal of Toxicology* 22(Suppl 1):1-35 2003
2. Lindqvist B, Sjögren I, Nordin R. Preparative fractionation of triglyceride mixtures according to acyl carbon number, using hydroxyalkoxypropyl Sephadex. *J. Lipid Res.* 1974 January;15(1):65-73.
3. Marten B, Pfeuffer M, Schrezenmeir J. Medium-chain triglycerides. *International Dairy Journal* 16 (2006) 1374-1382.
4. Traul K A, Driedger A, Ingle D L, Nakhasi D. Review of the toxicologic properties of medium-chain triglycerides. *Food Chem Toxicol.* 2000 January;38(1):79-98.
5. US FDA. http://www.accessdata.fda.gov/scripts/fdcc/?set=GRASNotices&id=449. Jul. 7, 2014

The invention claimed is:

1. A composition of medium-chain triglycerides comprising 5-45% C8 (caprylic acid), 25-31% C10 (capric acid), and at least 5-20% C12 (lauric acid), with less than 5% of the content being of other fatty acids.

2. The composition according to claim 1, comprising preferably at least 13% C8, at least 8% C10 and at least 5% C12, with less than 5% of the content being of other fatty acids.

3. The composition according to claim 1, comprising preferably at least 35% C8, at least 25% C10 and at least 20% C12, with less than 5% of the content being of other fatty acids.

4. The composition according to claim 1, derived entirely or in part from coconut.

5. The composition according to claim 1, derived entirely or in part from palm kernel.

6. The composition according to claim 1, wherein at least an antioxidant substance is added.

7. The composition according to claim 6, wherein the anti-oxidant is citric acid.

8. A thickening substance or gellant containing the composition according to claim 1.

9. The thickening substance or gellant according to claim 8, wherein the composition of medium-chain triglycerides comprising 5-45% C8 (caprylic acid), 25-31% C10 (capric acid), and at least 5-20% C12 (lauric acid), with less than 5% of the content being of other fatty acids, is incorporated in at least one of the substances selected from a group consisting of bentonite clays, fumed silica or magnesium aluminum silicates.

10. A food emulsifier containing the composition according to claim 1.

11. The food emulsifier according to claim 10, wherein the composition according to claim 1 is incorporated in at least one of the substances selected from a group consisting of distilled monolglycerides of stearic acid or oleic acid, polyglycerol fatty acid esters or polyethoxylated sorbitan esters.

12. A food product, a food supplement, a beverage, a cosmetic or a pharmaceutical product comprising the composition according to claim 1.

* * * * *